(12) United States Patent
De Carvalho et al.

(10) Patent No.: US 8,409,553 B2
(45) Date of Patent: Apr. 2, 2013

(54) COSMETIC COMPOSITION FOR THE HAIR WITH A WAXY EFFECT, IN AEROSOL FORM

(75) Inventors: Racquel De Carvalho, Clichy (FR); Françoise Pataut, Paris (FR)

(73) Assignee: L'Oreal, Paris (FR)

( * ) Notice: Subject to any disclaimer, the term of this patent is extended or adjusted under 35 U.S.C. 154(b) by 145 days.

(21) Appl. No.: 12/555,605

(22) Filed: Sep. 8, 2009

(65) Prior Publication Data

US 2010/0202997 A1 Aug. 12, 2010

Related U.S. Application Data

(63) Continuation of application No. 10/702,438, filed on Nov. 7, 2003, now abandoned.

(60) Provisional application No. 60/434,677, filed on Dec. 20, 2002.

(30) Foreign Application Priority Data

Nov. 8, 2002 (FR) ..................... 02 14075

(51) Int. Cl.
*A61Q 5/06* (2006.01)
(52) U.S. Cl. ..................... 424/70.11; 424/70.1
(58) Field of Classification Search .......... 424/70.1, 424/70.11
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,716,633 A | 2/1973 | Viout et al. | |
| 4,070,533 A | 1/1978 | Papantoniou et al. | |
| 4,128,631 A | 12/1978 | Lundmark et al. | |
| 4,137,208 A | 1/1979 | Elliott | |
| 4,282,203 A | 8/1981 | Jacquet et al. | |
| 5,320,836 A | 6/1994 | Singleton | |
| 5,639,448 A | 6/1997 | Galleguillos et al. | |
| 6,585,965 B1 | 7/2003 | Carballada et al. | |
| 6,635,240 B1 | 10/2003 | Bolich et al. | |
| 7,655,219 B2 | 2/2010 | Pataut et al. | |
| 2001/0003584 A1 | 6/2001 | Birkel et al. | |
| 2004/0170575 A1 | 9/2004 | Belli et al. | |

FOREIGN PATENT DOCUMENTS

| | | |
|---|---|---|
| FR | 1 222 944 | 6/1960 |
| FR | 1 564 110 | 4/1969 |
| FR | 1 580 545 | 9/1969 |
| FR | 2 265 782 | 10/1975 |
| FR | 2 350 384 | 12/1977 |
| FR | 2 357 241 | 2/1978 |
| FR | 2 439 798 | 5/1980 |
| GB | 839 805 | 6/1960 |
| JP | T-H08-505394 | 6/1996 |
| JP | A-H09-255534 | 9/1997 |
| JP | A-2000-026254 | 1/2000 |
| JP | A-2000-204025 | 7/2000 |
| LU | 75371 | 7/1976 |
| LU | 75370 | 2/1978 |
| WO | WO 94/15575 | 7/1994 |
| WO | WO 00/67709 | 11/2000 |

OTHER PUBLICATIONS

English language Derwent Abstract of FR 1 564 110, Apr. 18, 1969.
English language Derwent Abstract of FR 2 357 241, Feb. 3, 1978.
English language abstract of JP-A-2000-204025, Jul. 25, 2000.
English language abstract of JP-A-2000-026254, Jan. 25, 2000.
English language abstract of JP-A-H09-255534, Sep. 30, 1997.

*Primary Examiner* — Gina C Justice
(74) *Attorney, Agent, or Firm* — O'Brien Jones, PLLC

(57) ABSTRACT

The disclosure relates to a cosmetic composition for the hair, packaged in an aerosol device, comprising polyols in high concentration together with anionic fixing polymers. It further relates to a cosmetic method for the hair comprising the application of this composition to the hair, and to its use for imparting a waxy effect to the hair.

19 Claims, No Drawings

COSMETIC COMPOSITION FOR THE HAIR WITH A WAXY EFFECT, IN AEROSOL FORM

This application is a continuation of application Ser. No. 10/702,438, filed Nov. 7, 2003 now abandoned, which claims the benefit of U.S. Provisional Application No. 60/434,677, filed Dec. 20, 2002, both of which are incorporated herein by reference.

The present disclosure relates to a cosmetic composition for the hair, packaged in an aerosol device, comprising polyols in high concentration together with anionic fixing polymers. It further relates to a cosmetic method for the hair comprising the application of this composition to the hair, and to its use for imparting a waxy effect to the hair.

For the purposes of the present disclosure, "cosmetic compositions for the hair" are understood as meaning hair fixing and/or holding compositions, hair care compositions, hair conditioning compositions, such as compositions for imparting softness to the hair, or hair make-up compositions.

"Composition with a waxy effect" is understood as meaning a pasty composition for holding and/or fixing the individual hairs together by means of a certain slicking or greasing effect without the hardening effect of fixing sprays, while at the same time preserving the natural gloss of the hair.

The cosmetic composition for hair according to the disclosure can be used in a rinsed or leave-in application.

Hair styling compositions, such as lacquers and sprays, packaged in the form of an aerosol spray can be generally made up of a liquid phase comprising at least one film-forming polymer in a cosmetically acceptable alcoholic or aqueous-alcoholic medium, and a propellant, which can be a gas liquefied under reduced pressure or dissolved in the liquid phase.

The majority of hair styling products with a waxy effect are presented in the form of a more or less viscous paste which is applied to the hair by hand. In general, these products are packaged in tubes or in containers fitted with a lid.

It would be desirable to present this type of hair styling product in packaging that is easier to use.

In the hair product art, attempts are being made to manufacture aerosol lacquers containing reduced amounts of volatile organic compounds, such as ethanol, essentially for ecological reasons, while at the same time preserving good hair shaping and holding properties. A problem that may be posed by the search for such a product is to find cosmetic compositions that impart a waxy effect to the hair without exhibiting the disadvantages expressed above.

Surprisingly and unexpectedly, it has been discovered by the present inventors that it is possible to impart a waxy effect to the hair without detracting from its cosmetic properties, such as its natural softness, by using polyols in high concentration combined with anionic fixing polymers, packaged in aerosol form.

The present disclosure thus relates to a cosmetic composition for the hair, packaged in an aerosol device, comprising:
a) at least one anionic fixing polymer, present in an amount ranging from 0.5% to 10% by weight, based on the total weight of the aerosol composition,
b) at least one polyol with a molecular weight less than 500, present in an amount greater than 15% by weight, based on the total weight of the aerosol composition,
c) an aqueous-alcoholic or aqueous medium comprising at least 10% by weight of water, based on the total weight of the aerosol composition, and
d) at least one propellant gas present in an amount greater than or equal to 30% by weight, based on the total weight of the aerosol composition.

The present disclosure also relates to a hair styling method using the composition disclosed herein, packaged in an aerosol device.

Additional characteristics, features and advantages of the disclosure are discussed in the description and the various Examples which follow.

This disclosed combination of anionic fixing polymers and polyols affords aerosols with a low VOC content, for example, a VOC content less than or equal to 55%.

Without being bound by theory, it is believed by the present inventors that the waxy effect of the compositions disclosed herein is obtained by combining at least one polyol with a molecular weight below 500, in high concentration, with one or more anionic fixing polymers. The polyols provide the "slicking" or "greasy" aspect of waxes and the associated anionic fixing polymers provide the "stiffening of the grease", which enables the hair to be shaped and held in the desired configuration; waxes are completely absent from the formulation.

Anionic Fixing Polymer

The anionic fixing polymers useful in the compositions disclosed herein are polymers comprising groups chosen from derivatives of carboxylic, sulphonic and phosphoric acid groups, and have a number-average molecular weight ranging from 500 to 5,000,000.

The carboxylic acid groups can be chosen from unsaturated monocarboxylic and dicarboxylic acid monomers such as those of the formula

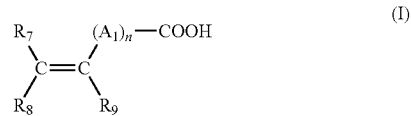

(I)

wherein
n is an integer ranging from 0 to 10,
$A_1$ is a methylene group, which can be optionally joined to the carbon atom of the unsaturated group, or to the adjacent methylene group when n is greater than 1, via a heteroatom such as oxygen or sulphur,
$R_7$ is chosen from a hydrogen atom, phenyl and benzyl groups,
$R_8$ is chosen from a hydrogen atom, lower alkyl and carboxyl groups, and
$R_9$ is chosen from a hydrogen atom, lower alkyl groups —$CH_2$—COOH, phenyl and benzyl groups.

In the formula given above, a lower alkyl group may denote, for example, a group having 1 to 4 carbon atoms, such as methyl or ethyl groups.

Non-limiting mention may be made of the following anionic fixing polymers with carboxylic acid groups according to the present disclosure:

A) Homopolymers and/or copolymers of acrylic and/or methacrylic acid or their salts, for example, the products sold under the name VERSICOL® E or K by ALLIED COLLOID and under the name ULTRAHOLD® by BASF, the acrylic acid/acrylamide copolymers sold in the form of their sodium salts under the name RETEN 421, 423 or 425 by HERCULES, and the sodium salts of polyhydroxycarboxylic acids.

B) Copolymers of acrylic or methacrylic acid with a monoethylenic monomer such as ethylene, styrene, vinyl esters and/or acrylic or methacrylic acid esters, optionally grafted onto a polyalkylene glycol such as polyethylene glycol, and optionally crosslinked. Such polymers are described, for example, in French Patent No. 1 222 944 and German Patent Application No. 2 330 956, the copolymers of this type containing an optionally N-alkylated and/or hydroxyalkylated acrylamide unit in their chain, such as those described for instance in Luxembourg Patent Applications Nos. 75370 and 75371, or marketed under the name QUADRAMER by AMERICAN CYANAMID. There may also be mentioned copolymers of acrylic acid and $C_1$-$C_4$-alkyl methacrylate and terpolymers of vinylpyrrolidone, acrylic acid and $C_1$-$C_{20}$-alkyl methacrylate, for example lauryl methacrylate, such as that marketed by ISP under the name ACRYLIDONE® LM, and methacrylic acid/ethyl acrylate/tert-butyl acrylate terpolymers such as the product marketed under the name LUVIMER® 100 P by BASF.

There may also be mentioned the methacrylic acid/acrylic acid/ethyl acrylate/methyl methacrylate copolymers in aqueous dispersion which are marketed under the name AMERHOLD® DR 25 by AMERCHOL.

C) Crotonic acid copolymers such as those comprising, in their chain, at least one unit chosen from vinyl acetate and propionate units and optionally at least one other monomer chosen from allyl esters, methallyl esters, vinyl ethers and vinyl esters of linear or branched, saturated carboxylic acids with a long hydrocarbon chain, such as those containing at least 5 carbon atoms, it optionally being possible for these polymers to be grafted or crosslinked, or at least one other monomer chosen from vinyl, allyl and methallyl esters of an alpha-carboxylic or alpha-cyclic carboxylic acid. Such polymers are described inter alia in French Patent Nos. 1 222 944, 1 580 545, 2 265 782, 2 265 781, 1 564 110 and 2 439 798. Commercial products belonging to this class are the resins 28-29-30, 26-13-14 and 28-13-10 marketed by National Starch.

D) Copolymers of mono-unsaturated $C_4$-$C_8$ carboxylic acids or anhydrides which may be selected from:

copolymers comprising (i) at least one entity chosen from maleic, fumaric and itaconic acids or anhydrides, and (ii) at least one monomer selected from vinyl esters, vinyl ethers, vinyl halides, phenylvinyl derivatives and acrylic acid and its esters, the anhydride groups of these copolymers optionally being monoesterified or monoamidated. Such polymers are described for instance in U.S. Pat. Nos. 2,047,398, 2,723,248 and 2,102,113 and GB Patent No. 839 805. Commercial products for example, may be those sold under the name GANTREZ® AN or ES by ISP.

copolymers comprising (i) at least one unit chosen from maleic, citraconic and itaconic anhydride units, and (ii) at least one monomer selected from allyl and methallyl esters, which may optionally comprise at least one group in their chain chosen from acrylamide, methacrylamide, alpha-olefin, acrylic acid ester, methacrylic acid ester, acrylic acid, methacrylic acid and vinylpyrrolidone groups,
the anhydride groups of these copolymers optionally being monoesterified or monoamidated.

These polymers are described for example in French Patents Nos. 2 350 384 and 2 357 241, assigned to L'Oréal.

E) Polyacrylamides comprising carboxylate groups.

Homopolymers and copolymers comprising sulphonic acid groups may be polymers comprising groups chosen from vinylsulphonic, styrenesulphonic, naphthalenesulphonic and acrylamidoalkylsulphonic acid units.

These polymers can be selected, for example, from:

polyvinylsulphonic acid salts with a molecular weight ranging from 1000 to 100,000, and copolymers with unsaturated comonomers such as acrylic or methacrylic acid and their esters, as well as acrylamide or its derivatives, vinyl ethers and vinylpyrrolidone.

polystyrenesulphonic acid salts such as the sodium salts sold for instance, under the names Flexan® 500 and Flexan® 130 by National Starch. These compounds are described in patent FR 2 198 719.

polyacrylamidesulphonic acid salts such as those mentioned in U.S. Pat. No. 4,128,631, for instance, the polyacrylamidoethylpropanesulphonic acid sold under the name COSMEDIA POLYMER HSP 1180 by Henkel.

The anionic polymers of the present disclosure can also be polycondensation products comprising at least one polyurethane sequence and at least one anionic group. These polycondensation products may optionally comprise a polysiloxane sequence. Among these polycondensation products, non-limiting examples include anionic polyurethanes, such as those marketed by BASF under the name Luviset PUR or Luviset Si PUR.

The anionic polymers of the present disclosure can also be polymers with a silicone skeleton and hydrocarbon grafts, and polymers with a hydrocarbon skeleton and silicone grafts, these polymers necessarily having at least one anionic group in their structure. The grafts may be fixed to the skeleton via a macromonomer. The polymer VS30 from 3M can be used as a polymer of this type.

As a further example, in the compositions according to the present disclosure, the anionic fixing polymer may be chosen from homopolymers and/or copolymers of acrylic and methacrylic acid and the salts thereof, crotonic acid copolymers, copolymers of monounsaturated $C_4$-$C_8$ carboxylic acids and/or anhydrides, polyacrylamides with carboxylate groups, homopolymers and/or copolymers with sulphonic acid groups, anionic polyurethanes and anionic grafted silicone polymers.

The hair styling composition contained in the aerosol device according to the present disclosure has a content of anionic fixing polymers for example, ranging from 0.5 to 10% by weight, such as ranging from 1 to 8% by weight, for instance, ranging from 2 to 6% by weight, based on the total weight of the aerosol composition.

Polyol

The polyols used in the compositions disclosed herein may be molecules comprising a $C_3$ to $C_{30}$ hydrocarbon chain which may optionally be interrupted by at least one heteroatom and is substituted by at least two hydroxyl groups. The molecular weight of the at least one polyol used herein is less than 500.

The hair styling composition contained in the aerosol device according to the present disclosure has a polyol content of greater than 15% by weight, and may have a polyol content for example, ranging from 15 to 55% by weight, such as, ranging from 15 to 40% by weight, for instance ranging from 20 to 35% by weight, based on the total weight of the aerosol composition.

Propylene glycol, glycerol, isoprene glycol, neopentyl glycol, hexylene glycol and polyethylene glycols may be mentioned as non-limiting examples of polyols which can be used herein.

In one aspect of the present disclosure, the hydrocarbon chain is not interrupted by a heteroatom; the number of carbon atoms in the hydrocarbon chain may be, for instance, less than 10, such as less than 8.

In another aspect of the present disclosure, the at least one polyol is chosen from propylene glycol and glycerol.

In yet another aspect of the present disclosure, the polyol is a glycol, i.e. it contains at least two adjacent carbon atoms each carrying at least one hydroxyl group.

Aqueous-Alcoholic Medium

The hair styling composition contained in the aerosol device disclosed herein has a water content of at least 10% by weight, and may have a water content for example, ranging from 10 to 54.5% by weight, such as, ranging from 10 to 45% by weight, for instance, ranging from 10 to 30% by weight, based on the total weight of the aerosol composition.

Propellant

According to the present disclosure, the propellant gas used may comprise at least one gas that may or may not be soluble in the composition, such as dimethyl ether, fluorinated or non-fluorinated hydrocarbons, the customary liquefied gases, or a mixture of these propellant gases. In one aspect of the disclosure, the propellant gas is dimethyl ether.

The hair styling composition contained in the aerosol device according to the present disclosure has a propellant gas content of greater than or equal to 30% by weight, and may have a propellant gas content for example, ranging from 30 to 50% by weight, such as ranging from 30 to 45% by weight, for instance ranging from 30 to 40% by weight, based on the total weight of the aerosol composition.

As an example, the composition may contain ethanol or isopropanol as the alcohol.

The hair styling composition can also comprise additives such as silicones in soluble, dispersed or microdispersed form, treating agents, hydrating agents other than the polyols of the invention, UV filters, acids, bases, plasticizers, solubilizers, preservatives, vitamins and provitamins, colorants, pigments, anionic, cationic, non-ionic or amphoteric surfactants, cationic, non-ionic or amphoteric fixing polymers, perfumes, corrosion inhibitors and mixtures thereof.

Those skilled in the art will take care to choose any additives and their amount so that they do not detract from the properties of the compositions of the present disclosure.

The compositions disclosed herein may be understood more clearly with the aid of the non-limiting Examples below.

EXAMPLES

Example 1

A 55% VOC aerosol spray was prepared which comprised the following in g/100 g of active substance:

| | |
|---|---|
| PVP/VA: | 1 |
| Ultra Hold Strong (BASF): | 4 |
| Aminomethylpropanol: | 0.48 |
| Propylene glycol: | 15 |
| Glycerol: | 15 |
| Perfume: | 0.2 |
| Water: | 10.32 |
| Alcohol: | 14 |
| DME: | 40 |

PVP/VA: marketed by BASF under the name Luviskol VA 64 Powder

Example 2

A VOC aerosol spray was prepared which comprised the following in g/100 g of active substance:

| | |
|---|---|
| Vinylpyrrolidone/Vinyl acetate (60/40): | 4 |
| 2-amino-2-methyl-1-propanol: | 0.4 |
| Glycerol: | 17.4 |
| Dimethyl ether: | 30 |
| Acrylic acid/Ethyl acrylate/n-tert-butylacrylamide: | 3 |
| Perfume: | 0.3 |
| Propylene glycol: | 11 |
| Polydimethyl/methylsiloxane oxyethylene (18/5): | 2.7 |
| Water: | 10 |
| Ethyl alcohol: | 21.2 |

Example 3

A VOC aerosol spray was prepared which comprised the following in g/100 g of active substance:

| | |
|---|---|
| Vinylpyrrolidone/Vinyl acetate (60/40): | 4 |
| 2-amino-2-methyl-1-propanol: | 0.4 |
| Glycerol: | 17.3 |
| Dimethyl ether: | 30 |
| Acrylic acid/Ethyl acrylate/n-tert-butylacrylamide: | 3 |
| Perfume: | 0.2 |
| Propylene glycol: | 11 |
| Polydimethyl/methylsiloxane oxyethylene (18/5): | 2.7 |
| Water: | 10 |
| Ethyl alcohol: | 21.4 |

Example 4

A VOC aerosol spray was prepared which comprised the following in g/100 g of active substance:

| | |
|---|---|
| Vinylpyrrolidone/Vinyl acetate (60/40): | 3 |
| 2-amino-2-methyl-1-propanol: | 0.3 |
| Glycerol: | 17.4 |
| Dimethyl ether: | 33 |
| Acrylic acid/Ethyl acrylate/n-tert-butylacrylamide: | 2 |
| Perfume: | 0.1 |
| Propylene glycol: | 10 |
| Polydimethyl/methylsiloxane oxyethylene (18/5): | 2.7 |
| Water: | 10.8 |
| Ethyl alcohol: | 20.7 |

What is claimed is:

1. A cosmetic aerosol spray composition for imparting a waxy effect to the hair, packaged in an aerosol device, comprising:
   a) at least one anionic fixing polymer present in an amount ranging from 0.5% to 10% by weight, based on the total weight of the aerosol composition,
   b) at least one polyol chosen from propylene glycol and glycerol, present in an amount greater than 15% by weight, based on the total weight of the aerosol composition,
   c) an aqueous-alcoholic or aqueous medium comprising at least 10% by weight of water, based on the total weight of the aerosol composition, and
   d) at least one propellant gas in an amount greater than or equal to 30% by weight, based on the total weight of the aerosol composition;
   wherein the aerosol spray composition has a volatile organic compound content of less than or equal to 55%.

2. The composition according to claim 1, wherein the at least one anionic fixing polymer is chosen from homopolymers and/or copolymers of acrylic and methacrylic acid and the salts thereof, crotonic acid copolymers, copolymers of monounsaturated $C_4$-$C_8$ carboxylic acids and/or anhydrides, polyacrylamides with carboxylate groups, homopolymers and/or copolymers with sulphonic acid groups, anionic polyurethanes and anionic grafted silicone polymers.

3. The composition according to claim 1, wherein the at least one anionic fixing polymer is present in an amount ranging from 0.5 to 10% by weight, based on the total weight of the aerosol composition.

4. The composition according to claim 3, wherein the at least one anionic fixing polymer is present in an amount ranging from 1 to 8% by weight, based on the total weight of the composition.

5. The composition according to claim 4, wherein the at least one anionic fixing polymer is present in an amount ranging from 2 to 6% by weight, based on the total weight of the aerosol composition.

6. The composition according to claim 1, wherein the at least one polyol is present in an amount ranging from 15 to 55% by weight, based on the total weight of the aerosol composition.

7. The composition according to claim 6, wherein the at least one polyol is present in an amount ranging from 15 to 40% by weight, based on the total weight of the aerosol composition.

8. The composition according to claim 7, wherein the at least one polyol is present in an amount ranging from 20 to 35% by weight, based on the total weight of the aerosol composition.

9. The composition according to claim 1, wherein the medium is an aqueous-alcoholic medium comprising an alcohol chosen from ethanol and isopropanol.

10. The composition according to claim 1, wherein the medium comprises from 10 to 54.5% by weight of water, based on the total weight of the composition.

11. The composition according to claim 10, wherein the medium comprises from 10 to 45% by weight of water, based on the total weight of the composition.

12. The composition according to claim 11, wherein the medium comprises from 10 to 30% by weight of water, based on the total weight of the composition.

13. The composition according to claim 1, wherein the at least one propellant gas is present in an amount ranging from 30 to 50% by weight, based on the total weight of the composition.

14. The composition according to claim 13, wherein the at least one propellant gas is present in an amount ranging from 30 to 45% by weight, based on the total weight of the composition.

15. The composition according to claim 14, wherein the at least one propellant gas is present in an amount ranging from 30 to 40% by weight, based on the total weight of the composition.

16. The composition according to claim 1, wherein the at least one propellant gas is dimethyl ether.

17. The composition according to claim 1, further comprising at least one additive chosen from silicones in soluble, dispersed or microdispersed form; treating agents; hydrating agents other than the polyols of the invention; UV filters; acids; bases; plasticizers; solubilizers; preservatives; vitamins and provitamins; colorants; pigments; anionic, cationic, non-ionic or amphoteric surfactants; cationic, non-ionic or amphoteric fixing polymers; perfumes; and corrosion inhibitors.

18. A cosmetic method for styling hair with a waxy effect, the method comprising, applying to hair a cosmetic aerosol spray composition comprising:
   a) at least one anionic fixing polymer present in an amount ranging from 0.5% to 10% by weight, based on the total weight of the aerosol composition,
   b) at least one polyol chosen from propylene glycol and glycerol, present in an amount greater than 15% by weight, based on the total weight of the aerosol composition,
   c) an aqueous-alcoholic or aqueous medium comprising at least 10% by weight of water, based on the total weight of the aerosol composition, and
   d) at least one propellant gas in an amount greater than or equal to 30% by weight, based on the total weight of the aerosol composition,
   wherein the composition is packaged in an aerosol device, and
   wherein the aerosol spray composition has a volatile organic compound content of less than or equal to 55%.

19. An aerosol spray device for imparting a waxy effect to hair, wherein the aerosol spray device contains a composition comprising:
   a) at least one anionic fixing polymer present in an amount ranging from 5% to 10% by weight, based on the total weight of the aerosol composition,
   b) at least one polyol chosen from propylene glycol and glycerol, present in an amount greater than 15% by weight, based on the total weight of the aerosol composition,
   c) an aqueous-alcoholic or aqueous medium comprising at least 10% by weight of water, based on the total weight of the aerosol composition, and
   d) at least one propellant gas in an amount greater than or equal to 30% by weight, based on the total weight of the aerosol composition;
   wherein the aerosol spray composition has a volatile organic compound content of less than or equal to 55%.

* * * * *